(12) United States Patent
Park et al.

(10) Patent No.: US 6,858,235 B2
(45) Date of Patent: Feb. 22, 2005

(54) ANTIOXIDANT COMPOSITION AND METHOD OF PREPARATION THEREOF

(75) Inventors: Mi-Hyoun Park, Seoul (KR); Nam-In Baek, Kyunggido (KR); Jae-Taek Han, Seoul (KR); Chang-Won Choi, Kwacheon-shi (KR)

(73) Assignee: Eromlife Co. Ltd., Seoul (KR)

( * ) Notice: Subject to any disclaimer, the term of this patent is extended or adjusted under 35 U.S.C. 154(b) by 33 days.

(21) Appl. No.: 10/289,457

(22) Filed: Nov. 7, 2002

(65) Prior Publication Data

US 2004/0028758 A1 Feb. 12, 2004

(30) Foreign Application Priority Data

Aug. 9, 2002 (KR) .................................. 10-2002-47048

(51) Int. Cl.$^7$ ............................................. A61K 35/78
(52) U.S. Cl. ....................................... 424/765; 424/773
(58) Field of Search ................................ 424/765, 773

(56) References Cited

U.S. PATENT DOCUMENTS

| 4,797,421 A | 1/1989 | Ariga et al. |
| 5,646,178 A | 7/1997 | Walker et al. |

FOREIGN PATENT DOCUMENTS

| KR | 1998-702533 | 7/1998 |
| KR | 2001-0010154 | 2/2001 |

*Primary Examiner*—Susan D. Coe
(74) *Attorney, Agent, or Firm*—Foley & Lardner LLP (57) ABSTRACT

The present invention relates to an antioxidant composition and a method of preparation thereof. In detail, the present invention relates to an antioxidant composition containing procyanidin B3 obtained from *Rosa multiflora*, and a preparation method for the antioxidant composition, comprising extraction of the underground part of *Rosa multiflora* with an organic solvent, followed by fractionation and purification of the extract by chromatography. The antioxidant composition of the present invention can be effectively used in treatment or prevention of various diseases due to oxidation by reactive oxygen species, maintenance of quality of food, and prevention of skin damages due to oxidation.

7 Claims, 5 Drawing Sheets

ANTIOXIDANT COMPOSITION AND METHOD OF PREPARATION THEREOF

TECHNICAL FIELD

The present invention relates to an antioxidant composition and a method of preparation thereof. More particularly, the present invention relates to an antioxidant composition containing procyanidin B3 obtained from *Rosa multiflora*, and a preparation method for the antioxidant composition, comprising extracting of the underground part of *Rosa multiflora* with an organic solvent, and fractionating and purifying the extract by chromatography.

BACKGROUND ART

Antioxidant activity is an activity that reduces production of reactive oxygen species in the body and at the same time, prevents oxidation that causes irrecoverable damages to cells. Ground-state or triplet oxygen can be activated as a result of exposure to environmental or biochemical factors such as enzymes, reduction metabolism, chemical compounds, pollutants and photochemical reactions, and transformed into reactive oxygen species (ROS) which have a high reactivity such as superoxide radicals, hydroxy radicals, and hydrogen peroxide, accordingly it results in irreversibly disrupting cell constituents. The actions of such reactive oxygen species can be reduced by antioxidant enzymes such as superoxide dismutase(SOD), catalase and peroxidase, and antioxidant substances such as vitamin C, vitamin E and glutathione, which all form the body's defense system. However, where disorder of such a defense mechanism in the body or exposure to excessive reactive oxygen species occurs, reactive oxygen species may irreversibly disrupt lipid, protein and DNA. As a result, various diseases inclusive of aging, cancer, multiple arteriosclerosis, arthritis and Parkinson's disease are caused.

Synthetic antioxidants such as BHA (butylated hydroxy anisole), BHT (butylated hydroxy toluene) and NDGA (nordihydro-guaiaretic acid) have been developed to date. By way of examples of natural antioxidants, there are antioxidant enzymes such as superoxide dismutase, peroxidase, catalase and glutathione peroxidase, and non-enzymatic antioxidant substances such as tocopherol (vitamin E), ascorbic acid (vitamin C), cartenoid and glutathione.

However, synthetic antioxidants may cause allergic reactions and oncogenesis due to their strong toxicity in the body, and be easily disrupted by heat due to temperature sensitivity. On the other hand, natural antioxidants are safer than synthetic antioxidants in the body but have the problem of weak effect. Therefore, the development of a new natural antioxidant having no problem with safety in use and also having excellent antioxidant activity has been required.

Meanwhile, procyanidin is a kind of proanthocyanidin present in various plants, which is known to be safe and have excellent antioxidant activity among natural antioxidants found to date. Proanthocyanidin is a group of compounds with a condensed tannin, that is, flavan-3-ol or flavan-3,4-diol which is bonded as a structural unit by condensation or polymerization. Of those, procyanidin includes all of the polymers ranging from dimers to oligomers of its backbone such as catechin, epicatechin, catechin gallate, epicatechin gallate, gallocatechin gallate or epigallocatechin gallate. Procyanidin is classified into various types according to backbone and bonding style. For example, procyanidin B3 has a catechin-(4α→8)-catechin structure, procyanidin B1 has an epicatechin-(4β→8)-catechin structure, procyanidin B2 has an epicatechin-(4β→8)-epicatechin structure and procyanidin B5 has an epicatechin-(4β→6)-epicatechin structure (Walter Feucht et al., *Z. Naturforsch.*, 54c, 942–945, 1999).

Procyanidin can be obtained by extracting various kinds of plant body with a solvent and fractionating and purifying the extract by chromatography, or can be isolated from wine or beer. Procyanidin was isolated by extraction with a solvent and chromatography from azuk beans (*Vigna angularis Ohwiet Ohashi*) (Toshiaki Ariga et al., *Agricultural Biological Chemistry*, Vol. 45, 2709–2712, 1981), bark of pine (*Loblolly pine*) (R. W. Hemingway et al., *Phytochemistry*, Vol. 22, 275–281, 1983) and root of knotgrass (*Polygonum multiflorum*) (Nonaka et al., *Phytochemistry*, Vol. 21, 429–432, 1982).

It was reported that procyanidin has the ability to bind protein and has anti-inflammatory effect. In particular, it was reported that catechin known as green tea tannin has excellent anticancer effect. U.S. Pat. No. 4,797,421 discloses the antioxidant effect of procyanidin. U.S. Pat. No. 5,646,178 discloses the antibacterial activity of procyanidin isolated from plant materials of the genus Vaccinium, especially cranberries. Korean Patent Application Laid-Open Publication No. 2001-10154 discloses the pharmaceutical composition containing procyanidin as an effective component for prevention or treatment of injury, tumor metastasis, paradental disease and arthritis associated with matrix metalloproteinase. Korean Patent Application Laid-Open Publication No. 1998-702533 discloses an anti-obesity agent containing procyanidin isolated from tamarind seed coat extract as an effective component.

However, until now, there are no reports that *Rosa multiflora* extract has antioxidant activity and contains procyanidin.

DISCLOSURE OF THE INVENTION

In the course of their studies on new natural antioxidants, the present inventors found that the extract obtained by extracting the underground part of *Rosa multiflora* with an organic solvent has antioxidant activity and contains procyanidin B3 compound, and completed the present invention based on such finding.

Therefore, it is an object of the present invention to provide a method for preparing an antioxidant composition, comprising the steps of (a) soaking and extracting the underground part of *Rosa multiflora* with ethanol or acetone; and (b) fractionating and purifying the extract obtained in the step (a) by chromatography.

It is another object of the present invention to provide an antioxidant composition containing the extract of *Rosa multiflora*, which is extracted from the underground part of *Rosa multiflora* with ethanol or acetone.

It is yet another object of the present invention to provide a method for preventing oxidation by contacting the antioxidant composition of the present invention with a substrate.

In accordance with one aspect of the present invention, the above and other objects can be accomplished by the provision of a method for preparing an antioxidant composition, comprising the steps of (a) soaking and extracting the underground part of *Rosa multiflora* with ethanol or acetone; and (b) fractionating and purifying the extract obtained in the step (a) by chromatography.

In accordance with another aspect of the present invention, there is provided an antioxidant composition containing the extract of *Rosa multiflora*, which is extracted from the underground part of *Rosa multiflora* with ethanol or acetone.

In accordance with yet another aspect of the present invention, there is provided a method for preventing oxidation by contacting the antioxidant composition of the present invention with a substrate.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

The present invention will be described as follows:

*Rosa multiflora* is a deciduous shrub of the family Rosaceae and is widely distributed at the base of mountains or riversides. Its fruit is used as a drug called "youngsil" in herbal medicine and was known to be effective for treatment of insomnia, amnesia, decreased sex drive, and edema. Its fruit is also used as a diuretic.

The active antioxidant composition of the present invention can be obtained by extracting the underground part of *Rosa multiflora* with ethanol or acetone. The ethanol extract can be fractionated using ethylacetate, water and butanol.

In case of using acetone as an extractant, an extract containing a large amount of an active antioxidant can be advantageously obtained without further solvent fractionation steps, unlike in case of using aqueous ethanol. On the other hand, in case of using aqueous ethanol as an extractant, extraction yield is high but many highly polar substances are extracted. In this regard, in order to facilitate the use of chromatography in the subsequent purification procedure, further steps are carried out, comprising adding ethylacetate and water to the ethanol extract to thereby obtain an ethylacetate fraction and a water fraction, and then adding butanol to the water fraction to thereby obtain a water fraction and a butanol fraction. Such an ethanol or aqueous ethanol extract has an advantage in use as a food raw material in the aspect of safety.

In accordance with one embodiment of the present invention, *Rosa multiflora* root is extracted with aqueous ethanol, and then distilled water and ethylacetate are added to the ethanol extract, thereby to fractionate into a water layer and an ethylacetate layer (x2). Butanol is added to the water layer thereby to fractionate into a water layer and a butanol layer (x2), resulting in an ethylacetate fraction, a butanol fraction and a water fraction being obtained. The obtained respective fractions all contained an active antioxidant component but the ethylacetate fraction showed the highest antioxidant activity and contained substances that can be easily isolated. This was demonstrated by developed TLC plate.

There is no particular limitation imposed on the ratio of the underground part of *Rosa multiflora* to extractant. However, based on 1 g fresh weight of the underground part of *Rosa multiflora*, the extractant can be used in an amount of 1 to 20 times (weight basis). In order to increase extraction efficiency, it is preferred that extraction is twice carried out using the extractant in an amount of 3 to 10 times (weight basis), based on 1 g fresh weight of the underground part of *Rosa multiflora*.

It is preferable for extraction to be carried out at room temperature under atmospheric pressure. An extraction time depends on an extraction temperature but is generally from 1 hour to 48 hours, preferably from 12 to 24 hours. Extraction efficiency can be further increased by stirring an extract with shaker at the time of extraction.

The underground part of *Rosa multiflora* to be used in extraction may be *Rosa multiflora* root or dried body thereof. In order to increase extraction efficiency, *Rosa multiflora* root or dried body thereof can be ground using a grinder.

The antioxidant activity of the *Rosa multiflora* extract of the present invention obtained according to the above method was measured according to the method for measuring antioxidant activity (The Korean Society of Food and Nutrition, Handbook for Experiments in Food and Nutrition, 651p, 2000; Blois, M. S., Nature, 4617:1198, 1958). As a result, it was demonstrated that the *Rosa multiflora* extract of the present invention has higher antioxidant activity than a conventional synthetic antioxidant, BHA, or a conventional natural antioxidant, tocopherol.

In addition, active fractions showing antioxidant activity can be obtained by fractionating and purifying the obtained *Rosa multiflora* extracts by chromatography. It is preferable to carry out silica gel column chromatography once or twice. Where active fractions obtained by silica gel column chromatography are further subjected to ODS column chromatography, more highly purified active fractions can be obtained. A mixture of chloroform and methanol or a mixture of methanol and distilled water can be used as a developing solvent at the time of chromatography. A flow rate of the developing solvent is generally from 5 Ml/hr to 1000 Ml/hr and preferably from 20 Ml/hr to 500 Ml/hr. The fractions eluted by chromatography are collected in flasks in the amount of 5 Ml to 100 Ml respectively. Active fractions showing antioxidant activity can be obtained by measuring antioxidant activities of the collected fractions. Antioxidant activity can be measured by a known method (The Korean Society of Food and Nutrition, Handbook for Experiments in Food and Nutrition, 651p, 2000; Blois, M. S., Nature, 4617:1198, 1958). It was confirmed that antioxidant activities of active fractions obtained according to one embodiment of the present invention are higher than those of a synthetic antioxidant, BHA, and a natural antioxidant, $\alpha$-tocopherol by the level of 2.7 and 3.8 times, respectively.

The present inventors investigated physical and chemical properties of the active fractions that were fractionated and purified by the above chromatography using hydrogen and carbon nuclear magnetic resonance spectrum. As a result, it was demonstrated that the active fractions contain procyanidin B3 of a catechin-($4\alpha \rightarrow 8$)-catechin structure as the following formula. Therefore, the antioxidant composition according to the present invention contains procyanidin B3 as an active component.

The present invention provides an antioxidant composition containing the extract of *Rosa multiflora*, which is extracted from the underground part of *Rosa multiflora* with ethanol or acetone. The antioxidant composition of the present invention can be prepared according to the method described above.

The antioxidant composition according to the present invention can be used as a pharmaceutical composition, a food composition and a cosmetic composition.

It is preferable for the pharmaceutical composition of the present invention to contain *Rosa multiflora* extract purified by column chromatography, but the extract obtained by extraction with a solvent can also be used.

The pharmaceutical composition according to the present invention can be administered orally or parenterally. The pharmaceutical composition according to the present invention can be administered, but is not limited to, in oral, intravenous, intramuscular, intraarterial, intramedullary, intradural, intracardiol, transdermal, subcutaneous, intraperitone al, intranasal, intrarectal, sublingual or topical route.

The pharmaceutical composition of the present invention can be prepared into suitable formulations by known methods for clinical administration. For example, the pharmaceutical composition of the present invention can be mixed with an inactive diluent or an edible carrier, sealed within hard or soft gelatin capsule, or compressed into tablet, and then can be administered orally. For oral administration, an active compound can be mixed with an excipient and then can be used in the form of edible tablet, buccal tablet, troche, capsule, elixir, suspension, syrup, wafer and the like. In addition, various formulations for injection or parenteral administration, or the like can be prepared by known or general methods.

An effective amount of the pharmaceutical composition of the present invention is 0.1 mg/kg to 500 mg/kg, preferably 1 mg/kg to 100 mg/kg and can be administered once to five times a day. However, a final administration amount and the number of administrations can be adjusted according to clinician's judgment after taking into consideration patient condition, age and the like.

The pharmaceutical composition according to the present invention can be effectively used for treatment or prevention of diseases caused by oxidation of cell constituents. Examples of such diseases include aging, cancer, multiple arteriosclerosis, arthritis and Parkinson's disease, but are not limited thereto.

The present invention provides a food composition containing the antioxidant composition of the present invention. The antioxidant composition according to the present invention has excellent antioxidant activity and effectively prevents deterioration of smell or flavor of food, fat rancidity, and discoloration of food due to oxidation. In this regard, incorporation of the antioxidant composition into various conventional foods makes it possible to preserve foods or maintain freshness and quality of foods for a long time. Furthermore, intake of foods containing the antioxidant composition reduces levels of oxidants in the body.

As used herein, the term "foods" include general foods as well as a drink (including an alcoholic drink), fruit and processed food thereof (for example, canned fruit, bottled food, jam and marmalade), fish, meat and processed food thereof (for example, ham, sausage and corned beef), bread and noodles (for example, thick wheat noodles, buckwheat noodles, instant noodles, spaghetti and macaroni), fruit juice, various drinks, cookies, wheat-gluten, milk products (for example, butter and cheese), edible vegetable oils, margarine, vegetable protein, retort foods, frozen food and various seasonings (for example, soybean paste, soy sauce and sauce).

The present invention provides a cosmetic composition containing the antioxidant composition of the present invention. In this case, the antioxidant composition of the present invention may be used per se or diluted as necessary. The cosmetic composition may be prepared in liquid or solid form by mixing the antioxidant composition with base ingredients, adjuvants and additives commonly used in the cosmetics field. Cosmetics in liquid or solid form include but are not limited to skin lotions, creams, lotions, and bath agents.

There are no particular limitation to the base ingredients, adjuvants and additives commonly used in the cosmetics field. By way of examples, water, alcohol, propylene glycol, stearic acid, glycerol, cetyl alcohol and liquid paraffin may be used.

The cosmetic composition according to the present invention is very useful for preventing skin damages due to oxidation, for example, spots (brown spots), freckles, skin fissure and UV damage (sun burning). It is also useful in maintaining quality of cosmetics by prevention of oxidation of cosmetics themselves.

The present invention also provides a method for preventing oxidation of a substrate by contacting the antioxidant composition with the substrate. As used herein, the term "substrate" means living body or skin of animal including humans. The pharmaceutical composition of the present invention may be administered internally to a live animal by various administration methods as described above. The cosmetic composition of the present invention is applied to skin, resulting in skin damages due to oxidation being prevented. The food composition of the present invention is ingested by animals, thereby oxidation of internal tissues being prevented.

EXAMPLES

The present invention will hereinafter be described more specifically by examples.

It is, however, to be borne in mind that the following examples are provided only for illustrations and thus the present invention is by no means limited to or by them.

Example 1

Preparation of Acetone Extract of *Rosa multiflora* Root

*Rosa multiflora* root was purchased from a shop for herbal medicine at Kyoungdong Market in Seoul, Korea. 15 L acetone was added to 3000 g (fresh weight) of the *Rosa multiflora* root and extraction was carried out at the room temperature for 24 hours. The extraction was repeated twice.

Acetone extract was concentrated and dried to yield 92 g.

Example 2

Preparation of Ethanol Extract of *Rosa multiflora* Root

15 L of 70% ethanol was added to 3000 g (fresh weight) of *Rosa multiflora* root and extraction was carried out at room temperature for 24 hours. The extraction was repeated twice. Aqueous ethanol extract was concentrated and dried to yield 146.4 g.

Example 3

Preparation of Ethylacetate Fraction, Butanol Fraction and Water Fraction of *Rosa multiflora* Root 1000 Ml of distilled water and 1000 Ml of ethylacetate were added to the aqueous ethanol extract obtained in example 2 to fractionate into a water layer and an ethylacetate layer (x2). 600 Ml of butanol was added to the water layer to fractionate into a water layer and a butanol layer (x2). Respective fractions were concentrated under reduced pressure to yield 76.9 g of ethylacetate fraction, 12.5 g of butanol fraction and 53.2 g of water fraction.

Example 4

Chromatography of Acetone Extract of *Rosa multiflora* Root

The acetone extract of *Rosa multiflora* root obtained in example 1 was in sequence subjected to silica gel chromatography and ODS chromatography to isolate and purify an active antioxidant substance. A silica gel (70–230 mesh, Merk) was suspended in chloroform-methanol solvent and then packed on a glass column (10×15 cm). The acetone extract of *Rosa multiflora* root obtained in example 1 was loaded in the glass column, followed by elution. Chloroform-methanol solvent as a developing solvent was used with a gradually increasing ratio of the methanol. The ratio of the chloroform-methanol solvent was gradually changed from 3:1 at 6000 Ml of the solvent to 2:1 at 2100 Ml of the solvent. Afterward, 2000 Ml of methanol only was used as a developing solvent. A flow rate of the developing solvent was set to be 200 Ml/hr and the fraction size was 50 Ml/flask. After chromatography, 170 eluted fractions were obtained and subjected to thin layer chromatography (hereinafter, referred to as "TLC"). The TLC plate was sprayed with 10% sulfuric acid and heated thereby to identify distribution of substances. As a result, twelve fractions containing similar component were collected. TLC plate (silica gel $F_{245}$, MERCK) was used as a stationary phase and the mixed solvent of chloroform and water (2:1) was used as a mobile phase. The antioxidant activities of twelve fractions were measured according to the method for measuring antioxidant activity using a free radical source (The Korean Society of Food and Nutrition, Handbook for Experiments in Food and Nutrition, 651p, 2000). As a result, in the sixth fraction, the highest antioxidant activity was observed and the yield was 6.16 g. This active fraction was again subjected to silica gel column chromatography according to the above method, yielding 3.11 g of an active antioxidant fraction. The active fraction thus obtained was loaded into a glass column (4.5×12 cm) packed with an ODS gel (40–63 μm, Merck) and the glass column was eluted with a mixed solvent of methanol and distilled water (methanol:distilled water=1:2, 1800 Ml) to purify 217 mg of a final active substance.

Example 5

Determination of Chemical Structure of Active Component Contained in *Rosa multiflora* Root Extract Chemical structure of the active antioxidant component contained in *Rosa multiflora* root extract was analyzed using a hydrogen and a carbon nuclear magnetic resonance spectrum. The physical and chemical properties thereof were also investigated.

Figure 1A:
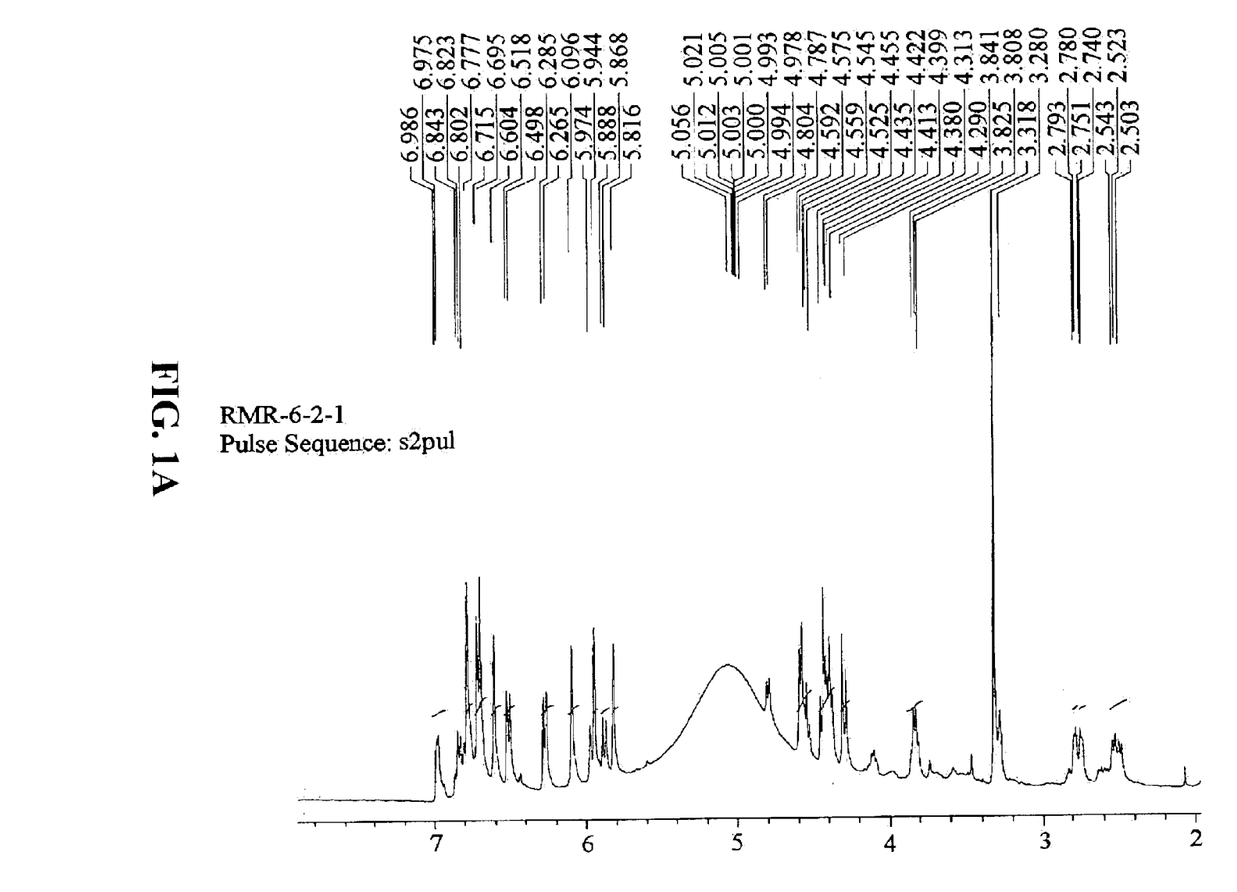
FIG. 1a is a hydrogen nuclear magnetic resonance spectrum of an active antioxidant component contained in *Rosa multiflora* root extract.
Figure 1B:
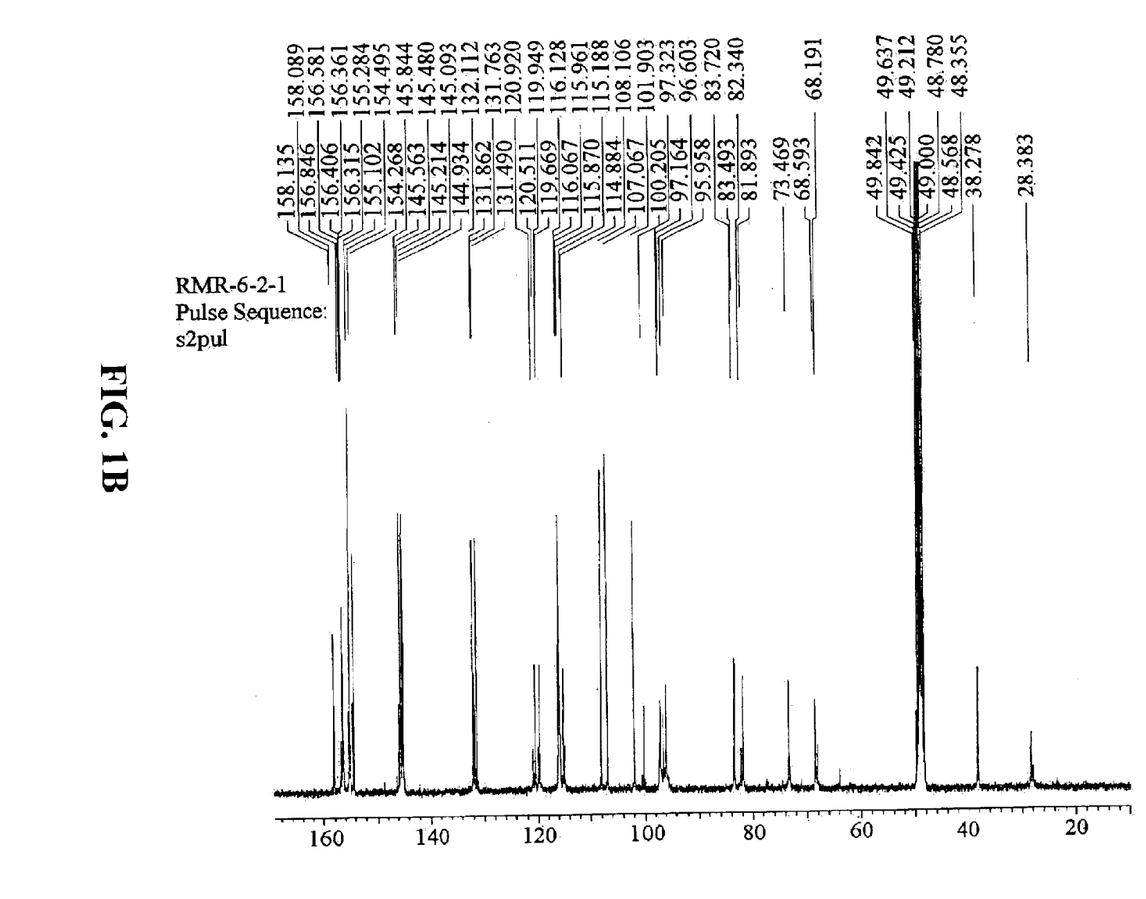
FIG. 1b is a carbon nuclear magnetic resonance spectrum of an active antioxidant component contained in *Rosa multiflora* root extract.

As a result, it was confirmed that the active antioxidant component is procyanidin B3 having a catechin-(4α→8)-catechin structure which is represented as the following structural formula. The physical and chemical properties thereof are as follows. The hydrogen and the carbon nuclear magnetic resonance spectrum thereof are shown in FIGS. 1*a* and 1*b* respectively.

1) Name: catechin-(4α→8)-catechin
2) Property: pale yellowish powder
3) Molecular Weight: 578
4) Structural Formula:

Example 6

Thin Layer Chromatography of *Rosa multiflora* Root Extracts Extracted with Organic Solvents and Column Chromatography Fractions Respective *Rosa multiflora* root extracts, solvent fractions and column chromatography fractions obtained in the examples 1 to 4 were subjected to TLC in order to confirm a fraction that contains the largest amount of procyanidin B3. Respective extracts and fractions were developed using TLC plate (silica gel $F_{245}$, MERCK) as a stationary phase and the mixed solvent of chloroform and water (2:1) as a mobile phase. 10% Sulfuric acid solution or 1,1-diphenyl-2-picrylhydrazyl (DPPH) solution was used for visualizing the developed TLC plate. The TLC plate was sprayed with 10% sulfuric acid solution and was heated, or was sprayed with DPPH solution. For the latter, presence of the active antioxidant substance was identified by spots where violet color of the DPPH solution is discolored.

Figure 2A:
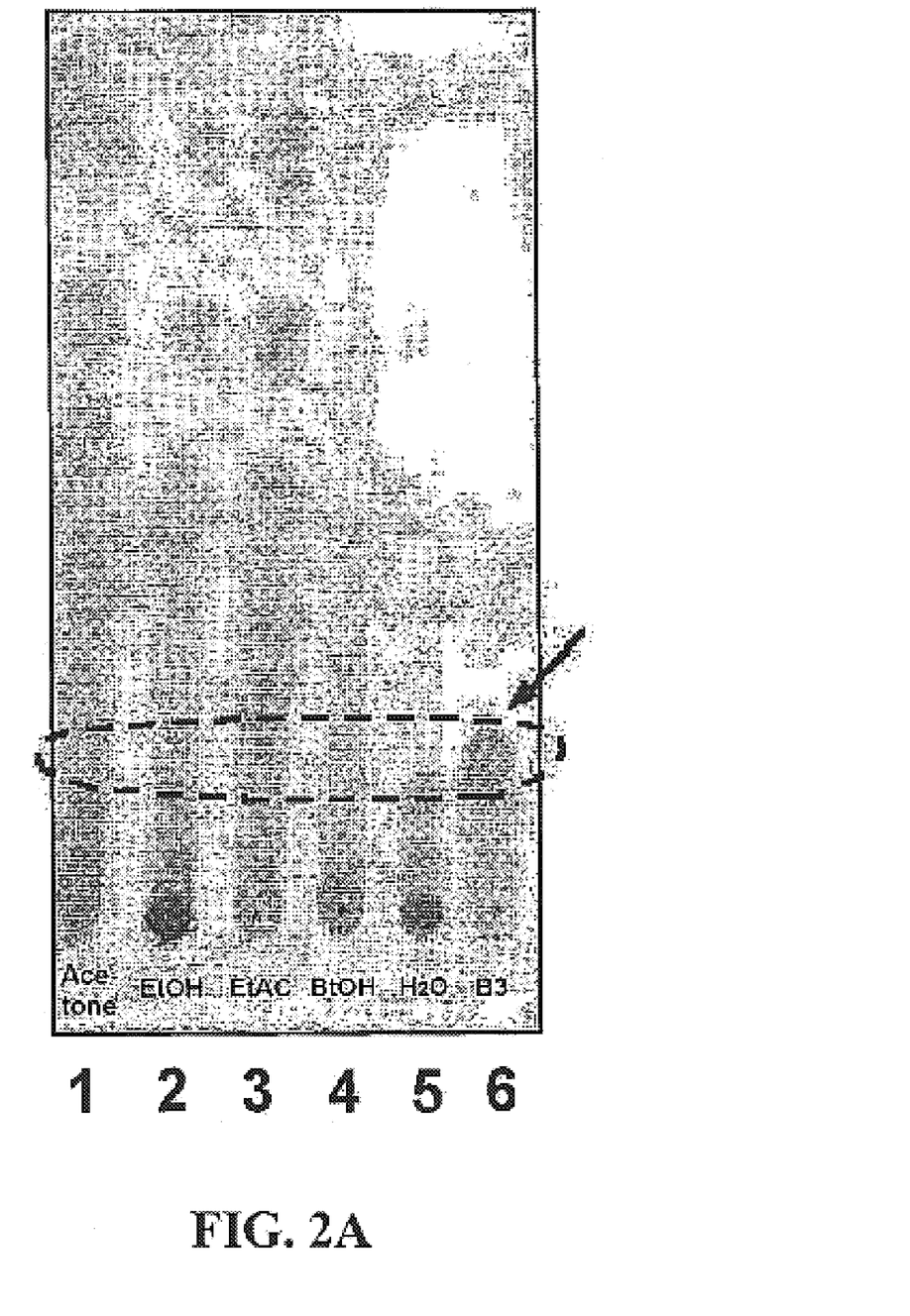
FIG. 2a is a component analysis result of *Rosa multiflora* root extract according to the present invention by thin layer chromatography, followed by color development with 10% sulfuric acid (1: acetone extract, 2: aqueous ethanol extract, 3: ethylacetate fraction, 4: butanol fraction, 5: water fraction, 6: procyanidin B3, Arrow: position of procyanidin B3)
Figure 2B:
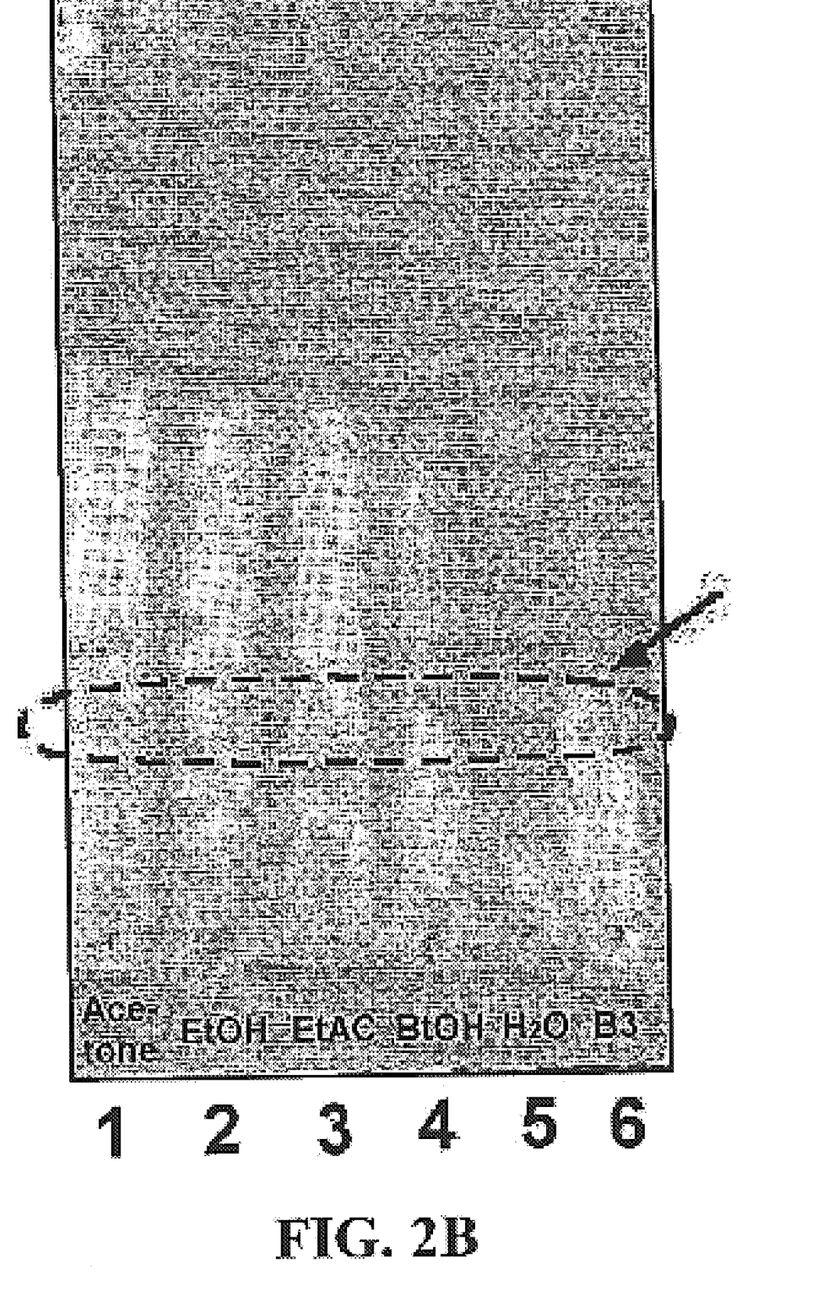
FIG. 2b is a component analysis result of *Rosa multiflora* root extract according to the present invention by thin layer chromatography, followed by spraying with 1,1-diphenyl-2-picrylhydrazyl (DPPH) solution (1: acetone extract, 2: aqueous ethanol extract, 3: ethylacetate fraction, 4: butanol fraction, 5: water fraction, 6: procyanidin B3, Arrow: position of procyanidin B3)

As a result, in case of using 10% sulfuric acid as a color developing agent, it was observed that the acetone extract, the ethanol extract and the ethylacetate fraction thereof contained procyanidin B3. The amount of the procyanidin B3 was estimated depending on a color intensity of the developed bands. As a result, it was observed that the acetone extract and the ethylacetate fraction contained a relatively large amount of procyanidin B3 (FIG. 2*a*). After observing spots that violet color of the DPPH solution is discolored, like in the case of color developing with sulfuric acid, it was confirmed that the acetone extract, the ethanol extract and the ethylacetate fraction thereof contained procyanidin B3 (FIG. 2*b*).

Figure 2C:
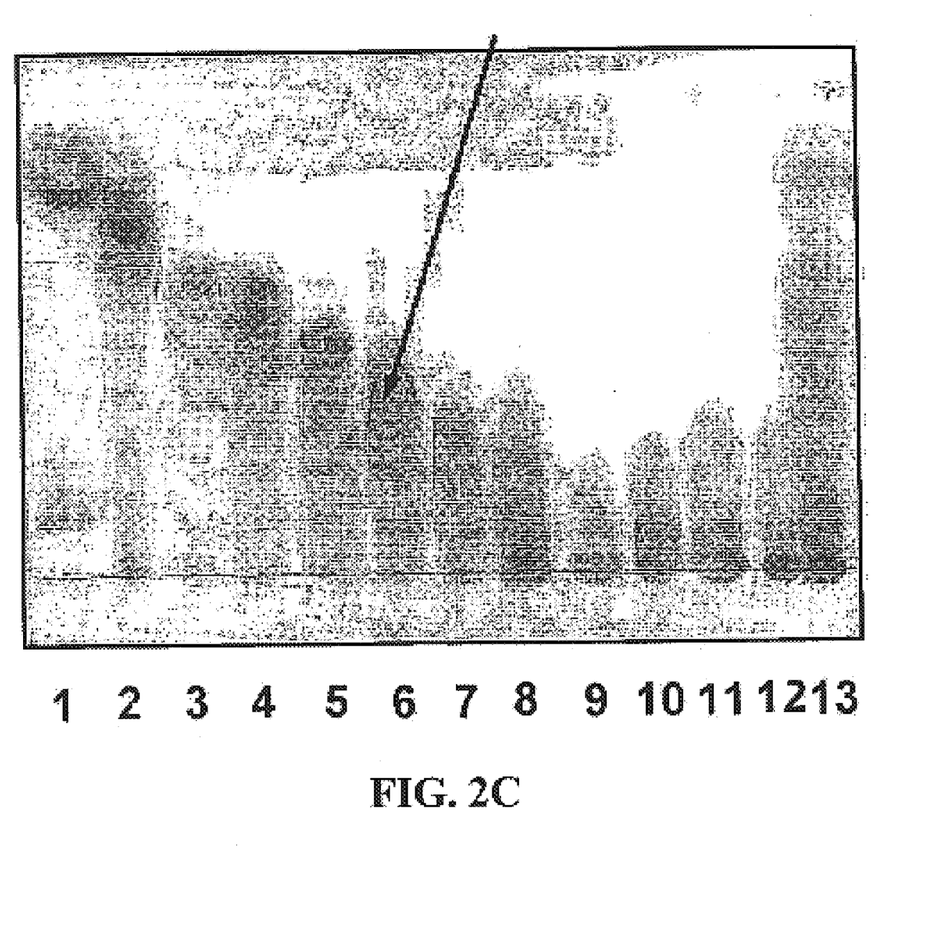
FIG. 2c is a component analysis result by column chromatography of the acetone extract of *Rosa multiflora* root, followed by thin layer chromatography of the obtained fractions (Arrow: position of procyanidin B3).

After TLC chromatography of twelve fractions isolated by column chromatography in example 4, it was observed that the sixth fraction contained a large amount of procyanidin B3 (FIG. 2*c*). This result is the same as that obtained in the method for measuring antioxidant activity using a free radical source in example 4.

Example 7

Measurement of Antioxidant Activity of *Rosa multiflora* Root Extract

Antioxidant activities of *Rosa multiflora* root extract obtained in example 1 and procyanidin B3, a final active substance obtained in example 4 were compared with those of a synthetic antioxidant BHA and a natural antioxidant α-tocopherol.

Antioxidant activity was measured according to the method for measuring antioxidant activity using a free radical source, 1,1-diphenyl-2-picrylhydrazyl (DPPH) (The Korean Society of Food and Nutrition, Handbook for Experiments in Food and Nutrition, 651p, 2000; Blois, M. S., Nature, 4617: 1198, 1958). 0.2 Ml Ethanol solution containing the *Rosa multiflora* root extract obtained in example 1, the final active substance obtained in example 4, BHA and tocopherol were poured in flasks with respective substances contained in varying amount of 2.0, 1.0, 0.5, 0.25, 0.125 and 0.063 mg/Ml. 0.8 Ml of DPPH (0.4 mM) solution and 3 Ml of ethanol were added, the reaction was carried out at the room temperature for 30 minutes and absorbance was measured at 517 nm. Antioxidant activity was expressed as a $RC_{50}$ value. The $RC_{50}$ represents the concentration of antioxidant (μg/Ml) required to achieve an absorbance equal to 50% of the absorbance of a control in which no antioxidants are contained.

As shown in Table 1, the antioxidant activity of *Rosa multiflora* root extract was relatively higher than those of BHA and α-tocopherol. The antioxidant activity of procyanidin B3 isolated from *Rosa multiflora* root extract was stronger than those of BHA and α-tocopherol by the level of 2.7 and 3.8 times respectively.

TABLE 1

Antioxidant activities of *Rosa multiflora* root extract and procyanidin B3 derived therefrom

| Substance | Antioxidant activity $RC_{50}$ (μg/Ml) |
|---|---|
| Procyanidin B3 | 3.4 |
| *Rosa multiflora* root extract | 7.6 |
| BHA | 9.2 |
| α-tocopherol | 13.0 |

Industrial Applicability

As apparent from the above description, the antioxidant composition according to the present invention can be effectively used in treatment or prevention of various diseases due to oxidation by reactive oxygen species, maintenance of quality of food, and prevention of skin damages due to oxidation.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for reducing oxidation, comprising contacting a substrate in need of protection from oxidation with a composition that comprises an extract of *Rosa multiflora*, which is extracted from the underground part of *Rosa multiflora* with ethanol or acetone.

2. The method according to claim 1, comprising administering said composition to a subject in need thereof.

3. The method according to claim 1, wherein the composition is one selected from a pharmaceutical composition, a food composition and a cosmetic composition.

4. The method according to claim 3, wherein the pharmaceutical composition is administered within the range of from 0.1 mg/kg to 500 mg/kg.

5. The method according to claim 2, comprising administering the composition internally or topically.

6. The method according to claim 1, wherein the underground part of *Rosa multiflora* is root or dried body thereof.

7. The method according to claim 1, wherein the extract of *Rosa multiflora* contains procyanidin B3 as the following formula:

* * * * *